(12) United States Patent
Kim

(10) Patent No.: US 10,231,764 B2
(45) Date of Patent: Mar. 19, 2019

(54) SYSTEM FOR FIXING CERVICAL VERTEBRAE, AN APPARATUS FOR FIXING CERVICAL VERTEBRAE AND A DRIVER USED FOR AN APPARATUS FOR FIXING CERVICAL VERTEBRAE

(71) Applicant: KYUNGPOOK NATIONAL UNIVERSITY INDUSTRY-ACADEMIC COOPERATION FOUNDATION, Daegu (KR)

(72) Inventor: Kyoung Tae Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 644 days.

(21) Appl. No.: 14/938,206

(22) Filed: Nov. 11, 2015

(65) Prior Publication Data

US 2016/0135850 A1    May 19, 2016

(30) Foreign Application Priority Data

Nov. 19, 2014  (KR) .................. 10-2014-0161998

(51) Int. Cl.
*A61B 17/80*  (2006.01)
*A61B 17/70*  (2006.01)
*A61B 17/88*  (2006.01)

(52) U.S. Cl.
CPC ...... *A61B 17/8042* (2013.01); *A61B 17/7059* (2013.01); *A61B 17/8877* (2013.01)

(58) Field of Classification Search
CPC .................. A61B 17/8033; A61B 17/8042
USPC .................. 606/280–299; 411/372.5, 372.6
See application file for complete search history.

(56) References Cited

U.S. PATENT DOCUMENTS

| | | | |
|---|---|---|---|
| 4,027,932 A | 6/1977 | Kunkel et al. |
| 4,359,318 A | 11/1982 | Gittleman |
| 4,474,516 A | 10/1984 | Schiefer |
| 4,678,383 A | 7/1987 | Bergner |
| 5,127,407 A | 7/1992 | Tan |
| 5,265,504 A | 11/1993 | Fruhm |
| 6,258,089 B1 | 7/2001 | Campbell et al. |
| 6,290,701 B1 | 9/2001 | Enayati |
| 6,402,757 B1 | 6/2002 | Moore, III et al. |
| 6,436,100 B1 | 8/2002 | Berger |

(Continued)

FOREIGN PATENT DOCUMENTS

| | | |
|---|---|---|
| JP | 2011-139901 A | 7/2011 |
| JP | 2014-517739 A | 7/2014 |

(Continued)

*Primary Examiner* — Eric S Gibson
(74) *Attorney, Agent, or Firm* — Novick, Kim & Lee, PLLC; Sang Ho Lee

(57) ABSTRACT

A fixing apparatus for cervical vertebrae in which in which a fixing plate is made to be in proximity with cervical vertebrae and screws are inserted into the cervical vertebrae through screw holes formed in the fixing plate, includes an opening and closing member that opens and closes the screw holes while being moved between a closing position for covering the screw holes and an opening position for opening the screw hole on the fixing plate.

16 Claims, 6 Drawing Sheets

(56) References Cited

U.S. PATENT DOCUMENTS

| | | | |
|---|---|---|---|
| 6,652,525 B1 * | 11/2003 | Assaker | A61B 17/7059 606/296 |
| 6,778,861 B1 | 8/2004 | Liebrecht et al. | |
| 7,029,472 B1 * | 4/2006 | Fortin | A61B 17/7014 606/105 |
| 7,194,314 B1 | 3/2007 | Richter et al. | |
| 7,235,100 B2 | 6/2007 | Martinek | |
| 7,302,298 B2 | 11/2007 | Lowry et al. | |
| 7,662,154 B2 * | 2/2010 | Ribeiro | A61B 17/1604 606/289 |
| 8,057,521 B2 * | 11/2011 | Smisson, III | A61B 17/8042 606/281 |
| 8,419,777 B2 * | 4/2013 | Walker | A61B 17/8033 606/289 |
| 8,454,667 B2 * | 6/2013 | Humphreys | A61B 17/8042 606/286 |
| 8,628,325 B2 | 1/2014 | Vachtenberg | |
| 8,758,347 B2 * | 6/2014 | Weiner | A61B 17/8009 606/282 |
| 8,906,077 B2 * | 12/2014 | Bush, Jr. | A61B 17/8042 606/296 |
| 8,932,335 B2 * | 1/2015 | Humphreys | A61B 17/7059 606/294 |
| 8,940,030 B1 * | 1/2015 | Stein | A61B 17/7059 606/294 |
| 9,265,531 B2 * | 2/2016 | Ziolo | A61B 17/7059 |
| 9,629,664 B2 * | 4/2017 | Altarac | A61B 17/7059 |
| 9,775,652 B2 * | 10/2017 | Altarac | A61B 17/7058 |
| 9,918,749 B2 * | 3/2018 | Altarac | A61B 17/7059 |
| 9,918,760 B2 * | 3/2018 | Bush, Jr. | A61B 17/8042 |
| 2002/0151899 A1 | 10/2002 | Bailey et al. | |
| 2003/0187440 A1 * | 10/2003 | Richelsoph | A61B 17/7059 606/287 |
| 2004/0220571 A1 * | 11/2004 | Assaker | A61B 17/7059 606/296 |
| 2004/0243207 A1 | 12/2004 | Olson et al. | |
| 2004/0267361 A1 | 12/2004 | Donnelly et al. | |
| 2005/0059972 A1 | 3/2005 | Biscup | |
| 2005/0192577 A1 * | 9/2005 | Mosca | A61B 17/1615 606/86 B |
| 2005/0261689 A1 * | 11/2005 | Lin | A61B 17/8042 606/296 |
| 2006/0161157 A1 * | 7/2006 | Mosca | A61B 17/1615 606/294 |
| 2006/0217721 A1 * | 9/2006 | Suh | A61B 17/8042 606/295 |
| 2006/0235410 A1 | 10/2006 | Ralph et al. | |
| 2006/0247639 A1 * | 11/2006 | Anderson | A61B 17/8042 606/281 |
| 2006/0293670 A1 * | 12/2006 | Smisson, III | A61B 17/8042 606/250 |
| 2007/0233071 A1 | 10/2007 | Dewey et al. | |
| 2008/0161864 A1 | 7/2008 | Beck et al. | |
| 2008/0221624 A1 | 9/2008 | Gooch | |
| 2009/0125072 A1 | 5/2009 | Neubardt | |
| 2009/0318970 A1 | 12/2009 | Butler et al. | |
| 2010/0036467 A1 | 2/2010 | Kraus et al. | |
| 2010/0049256 A1 * | 2/2010 | Jeon | A61B 17/7059 606/289 |
| 2010/0106198 A1 | 4/2010 | Adcox et al. | |
| 2010/0121383 A1 * | 5/2010 | Stanaford | A61B 17/8042 606/280 |
| 2011/0022097 A1 * | 1/2011 | Walker | A61B 17/8033 606/296 |
| 2011/0029023 A1 * | 2/2011 | Tornier | A61B 17/8042 606/289 |
| 2011/0106159 A1 * | 5/2011 | Nazeck | A61B 17/7059 606/246 |
| 2011/0144702 A1 | 6/2011 | Leroux et al. | |
| 2011/0230885 A1 * | 9/2011 | Weiner | A61B 17/8009 606/71 |
| 2011/0264151 A1 | 10/2011 | Davis et al. | |
| 2012/0185001 A1 | 7/2012 | Nayet et al. | |
| 2012/0232595 A1 * | 9/2012 | Holschlag | A61B 17/8042 606/280 |
| 2012/0265258 A1 | 10/2012 | Garvey | |
| 2012/0271363 A1 | 10/2012 | Luxon et al. | |
| 2012/0289978 A1 * | 11/2012 | Jacob | A61B 17/8042 606/151 |
| 2013/0023936 A1 * | 1/2013 | Altarac | A61B 17/7059 606/279 |
| 2013/0041413 A1 * | 2/2013 | Sun | A61B 17/8047 606/296 |
| 2013/0231704 A1 | 9/2013 | Larroque-Lahitette | |
| 2013/0304067 A1 * | 11/2013 | Hess | A61B 17/8009 606/71 |
| 2013/0325074 A1 * | 12/2013 | Ziolo | A61B 17/7059 606/290 |
| 2014/0066997 A1 * | 3/2014 | Humphreys | A61B 17/7059 606/294 |
| 2015/0134013 A1 * | 5/2015 | Paul | A61B 17/8042 606/294 |
| 2015/0201982 A1 * | 7/2015 | Altarac | A61B 17/7059 606/246 |
| 2015/0216573 A1 * | 8/2015 | Chin | A61B 17/7059 606/279 |
| 2015/0230838 A1 * | 8/2015 | Lazoglu | A61B 17/8009 606/71 |
| 2016/0135850 A1 * | 5/2016 | Kim | A61B 17/7059 606/296 |
| 2016/0166295 A1 * | 6/2016 | Ziolo | A61B 17/7059 606/290 |
| 2016/0206351 A1 * | 7/2016 | Eom | A61B 17/80 |

FOREIGN PATENT DOCUMENTS

| | | |
|---|---|---|
| KR | 1999-0035953 A | 5/1999 |
| KR | 10-2002-0082009 A | 10/2002 |
| KR | 10-2004-0001287 A | 1/2004 |
| KR | 1020040001287 A | 1/2004 |
| KR | 20-0367241 Y1 | 11/2004 |
| KR | 10-2005-0023111 A | 3/2005 |
| KR | 10-2007-0026472 A | 3/2007 |
| KR | 10-2007-0112200 A | 11/2007 |
| KR | 10-2008-0059920 A | 7/2008 |
| KR | 10-0850322 B1 | 8/2008 |
| KR | 10-2008-0105506 A | 12/2008 |
| KR | 10-0872529 B1 | 12/2008 |
| KR | 10-2009-0015933 A | 2/2009 |
| KR | 10-2009-0111774 A | 10/2009 |
| KR | 10-2010-0124709 A | 11/2010 |
| KR | 10-2012-0039622 A | 4/2012 |
| KR | 10-2012-0040309 A | 4/2012 |
| KR | 10-2012-0052265 A | 5/2012 |
| KR | 10-1142895 B1 | 5/2012 |
| KR | 10-2012-0057758 A | 6/2012 |
| KR | 10-2013-0004669 A | 1/2013 |
| KR | 10-2013-0015081 A | 2/2013 |
| KR | 10-2013-0016303 A | 2/2013 |
| KR | 10-1331429 B1 | 11/2013 |
| KR | 10-2014-0003938 A | 1/2014 |
| KR | 10-2014-0018796 A | 2/2014 |
| KR | 10-2014-0052320 A | 5/2014 |
| KR | 10-1413732 B1 | 7/2014 |
| KR | 10-2015-0120105 A | 10/2015 |
| WO | 2008/146981 A1 | 12/2008 |
| WO | 2009/105106 A2 | 8/2009 |

* cited by examiner

SYSTEM FOR FIXING CERVICAL VERTEBRAE, AN APPARATUS FOR FIXING CERVICAL VERTEBRAE AND A DRIVER USED FOR AN APPARATUS FOR FIXING CERVICAL VERTEBRAE

INCORPORATION BY REFERENCE

The instant application claims benefit of priority from Korean Patent Application No. 10-2014-0161998, filed on Nov. 19, 2014, the entire content of which is hereby incorporated by reference.

BACKGROUND

1. Field of the Invention

The present invention relates to a fixing system for cervical vertebrae, and a fixing apparatus for cervical vertebrae and a driver used for the fixing apparatus for the cervical vertebrae, and more particularly, to a fixing system for the cervical vertebrae which includes an opening and closing member for opening and closing screw holes of a cervical vertebrae-fixing plate and a driver for moving the opening and closing member.

2. Discussion of Related Art

In general, cervical vertebrae are the seven vertebrae positioned at the top of the spine and between the skull and the spine, and most cervical vertebrae are small and flat, and a foramen through which the vertebral artery (except the seventh cervical vertebrae), the veins, and the cervical sympathetic trunk pass is present in each transverse process.

In addition, motor nerves which carry command information from the brain to the body parts such as legs and arms and sensory nerves which carry sensory information from the legs and arms and each body organ to the brain are constituted in the spinal cord and pass through the spinal canal present in the cervical vertebrae, and autonomic nerves which control heartbeat, breathing, and digestive functions pass in front of the cervical vertebrae and arteries which supply blood to the cerebrum pass on both sides of the cervical vertebrae.

The cervical vertebrae having the above-described structure and functions may be damaged or deformed in a curved state thereof due to external impact caused by accidents or twisted posture that continues for a long time, and in this instance, a gap between neck bones constituting the cervical vertebrae is narrowed to press the nerves so that slight pain may be initially felt, and in the mid and late stages, it is attended by symptoms in which the body is paralyzed in addition to severe pain. As a result, a disorder such as cervical disc disease, cervical hernial disc, cervical spondylosis myelopathy, cervical fracture and dislocation, a tumor, kyphotic deformity, and the like may be generated.

In the most common method for cervical vertebrae surgeries, a vertebral body of the disc in which a lesion is caused is removed, an artificial implant is inserted between the cervical vertebrae, and then a cervical vertebrae-fixing plate is fixed to the front side of the inserted artificial implant, and in this instance, a screw is inserted into the cervical vertebrae through screw holes formed in the cervical vertebrae-fixing plate (see Korean Patent Application No. 10-2002-0036430).

However, there are problems such as the inserted screw loosening to cause damage to the esophagus after the surgery, and therefore there has been a demand for a loosening prevention member for preventing the loosening of the screw, and when the screw is required to be intentionally removed due to the easiness of the operation of a member for preventing the loosening of the screw, there has been a demand for easily moving the loosening prevention member from the screw which should be removed.

In order to address these problems, a loosening prevention member that prevents the loosening of the screw inserted into the cervical vertebrae and is easily moved so that the screw is easily removed upon the removal of the inserted screw has emerged.

SUMMARY OF THE INVENTION

The present invention is directed to a fixing system for cervical vertebrae, which may include a loosening prevention member that can prevent the loosening of a screw inserted into the cervical vertebrae and be easily moved only with a simple operation so that the inserted screw may be easily removed.

Additional aspects of the invention will be set forth in part in the description which follows and, in part, will be obvious from the description, or may be learned by practice of the invention.

According to an aspect of the present invention, there is provided a fixing apparatus for cervical vertebrae, in which a fixing plate is made to be in proximity with cervical vertebrae and screws are inserted into the cervical vertebrae through screw holes formed in the fixing plate, including, an opening and closing member that opens and closes the screw holes while being moved between a closing position for covering the screw holes and an opening position for opening the screw hole on the fixing plate.

According to another aspect of the present invention, there is provided a fixing system for cervical vertebrae including, a fixing apparatus for cervical vertebrae in which a fixing plate is made to be in proximity with cervical vertebrae and screws are inserted into the cervical vertebrae through screw holes formed in the fixing plate, and a driver that moves opening and closing members that open and close the screw holes while being moved between a closing position for covering the screw holes and an opening position for opening the screw holes on the fixing plate, wherein the opening and closing members include covering portions for covering the screw holes and rack portions which are branched from the covering portions and have teeth thereon, and the driver is a pinion driver having a pinion-shaped front end portion and when the pinion-shaped front end portion of the pinion driver is engaged with the teeth of the rack portion and then rotated, the rack portion is moved so that each of the opening and closing members is moved between the closing position and the opening position on the fixing plate.

According to still another aspect of the present invention, there is provided a pinion driver that is used for a fixing apparatus for cervical vertebrae in which a fixing plate is made to be in proximity with cervical vertebrae and screws are inserted into the cervical vertebrae through screw holes formed in the fixing plate, and has a pinion-shaped front end portion, wherein the fixing apparatus for cervical vertebrae includes opening and closing members that open and close the screw holes while being moved between a closing position for covering the screw holes and an opening position for opening the screw holes on the fixing plate, the opening and closing members include covering portions for covering the screw holes and rack portions which are branched from the covering portions and have teeth thereon, and when the front end portion of the pinion driver is engaged with the teeth of the rack portion and then rotated, the rack portion is moved so that each of the opening and closing members is moved between the closing position and the opening position on the fixing plate.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
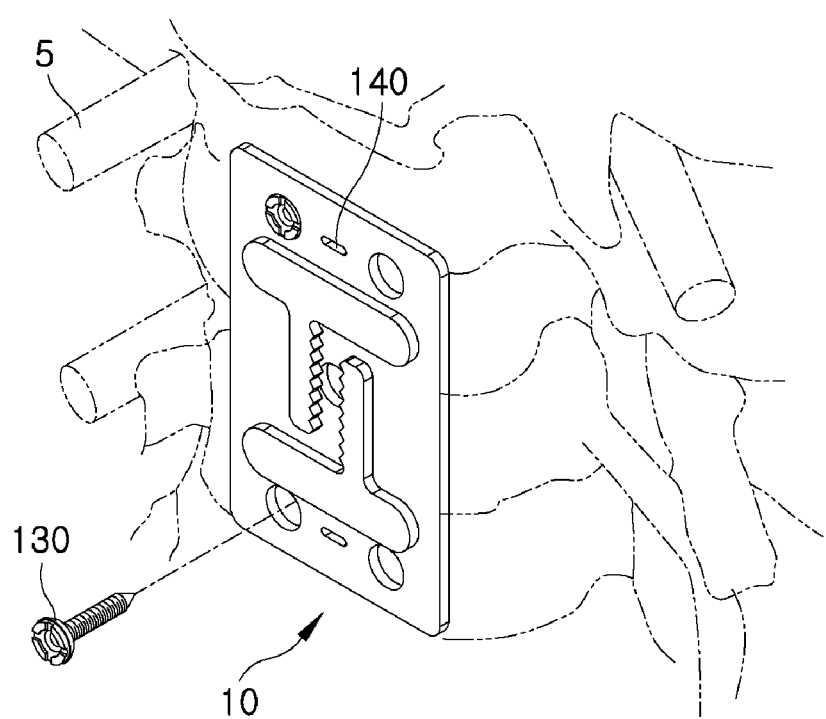
FIG. 1 shows a state in which a fixing apparatus for cervical vertebrae according to an embodiment of the present invention is mounted in the cervical vertebrae.

Hereinafter, preferred embodiments according to the present invention will be described with reference to the accompanying drawings.

However, the embodiments of the present invention can be modified in many different forms and the scope of the present invention is not limited to the embodiments described below. In addition, the embodiments of the present invention are provided to more completely explain the present invention to those skilled in the art. The present invention will only be defined by the scope of claims. The same reference numerals throughout the specification refer to like elements.

Terms used in the present specification are intended to illustrate the embodiments, and are not intended to limit the invention. In addition, as used herein, the singular forms "a," "an," and "the" are intended to include the plural forms, including "at least one," unless the content clearly indicates otherwise. In the specifications, it should be understood that the terms "comprising," or "including" when used in these specifications, specify the presence of stated elements, steps, and operations, but do not preclude the presence or addition of one or more other elements, steps and operations thereof.

Figure 2:
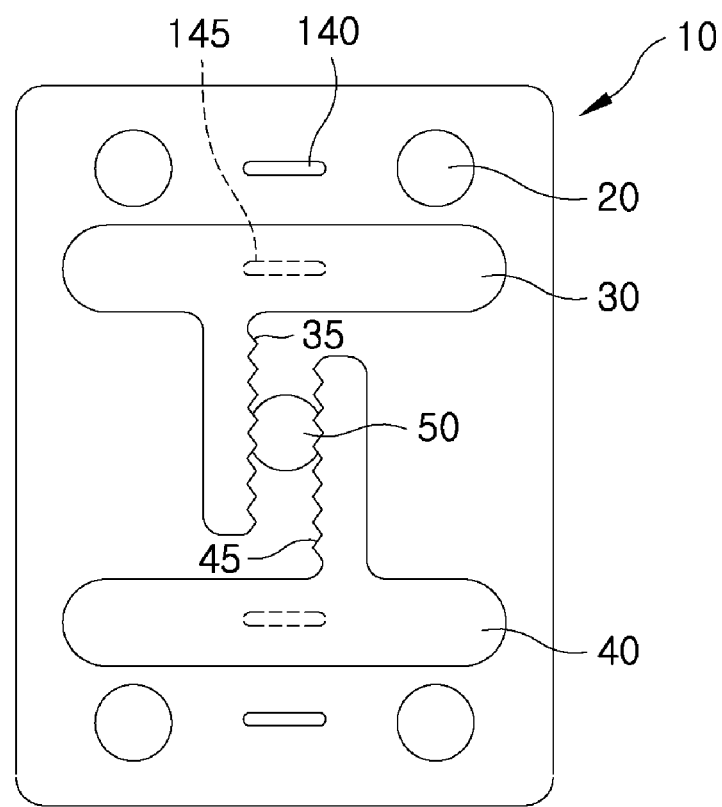
FIG. 2 shows a state in which screw holes of a fixing apparatus for cervical vertebrae according to an embodiment of the present invention are opened.
Figure 3:
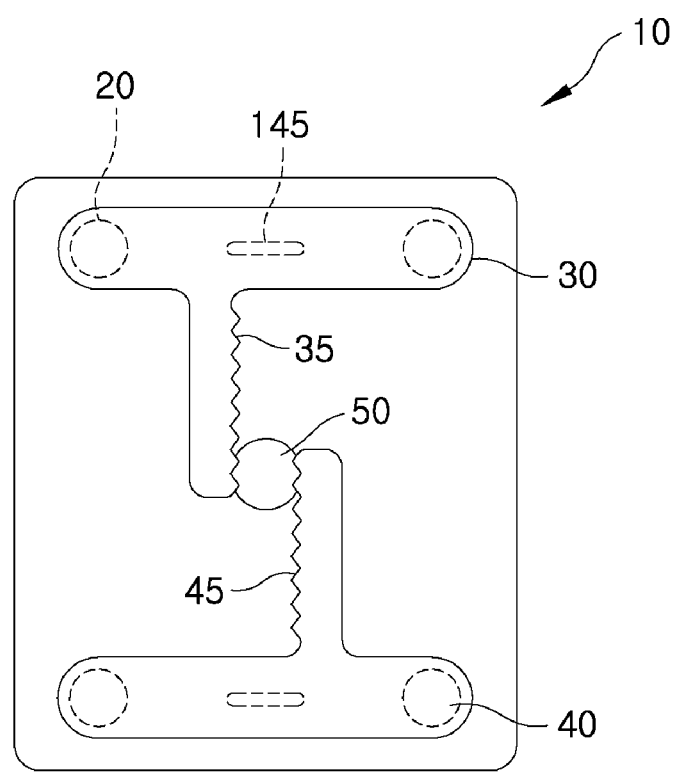
FIG. 3 shows a state in which screw holes of a fixing apparatus for cervical vertebrae according to an embodiment of the present invention are shielded.
Figure 4:
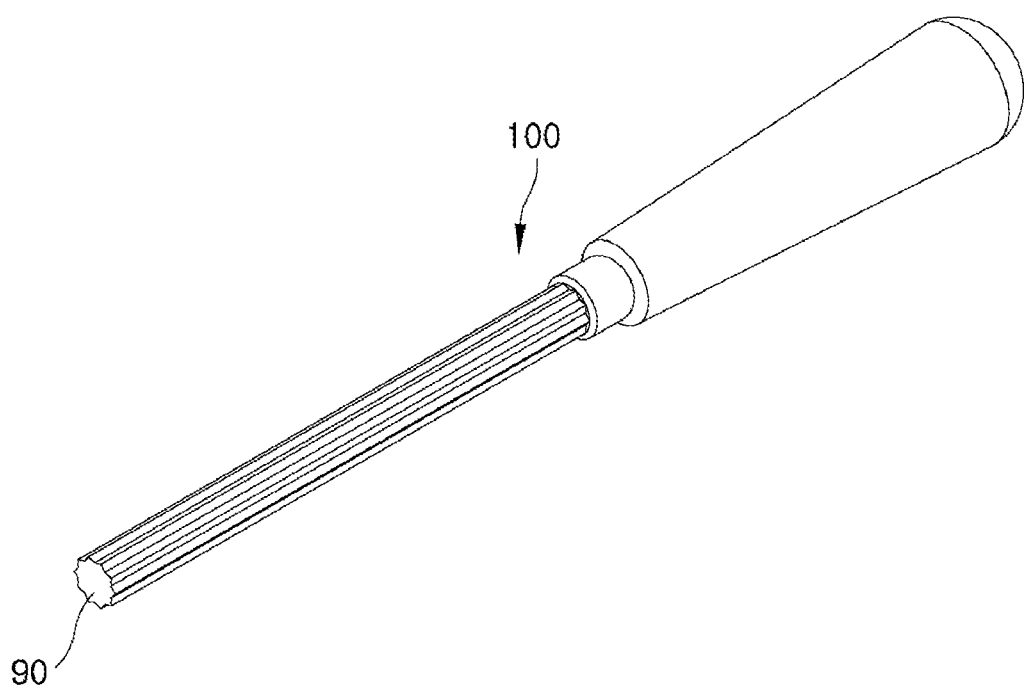
FIG. 4 is a perspective view showing a driver used for a fixing apparatus for cervical vertebrae according to an embodiment of the present invention.
Figure 5:
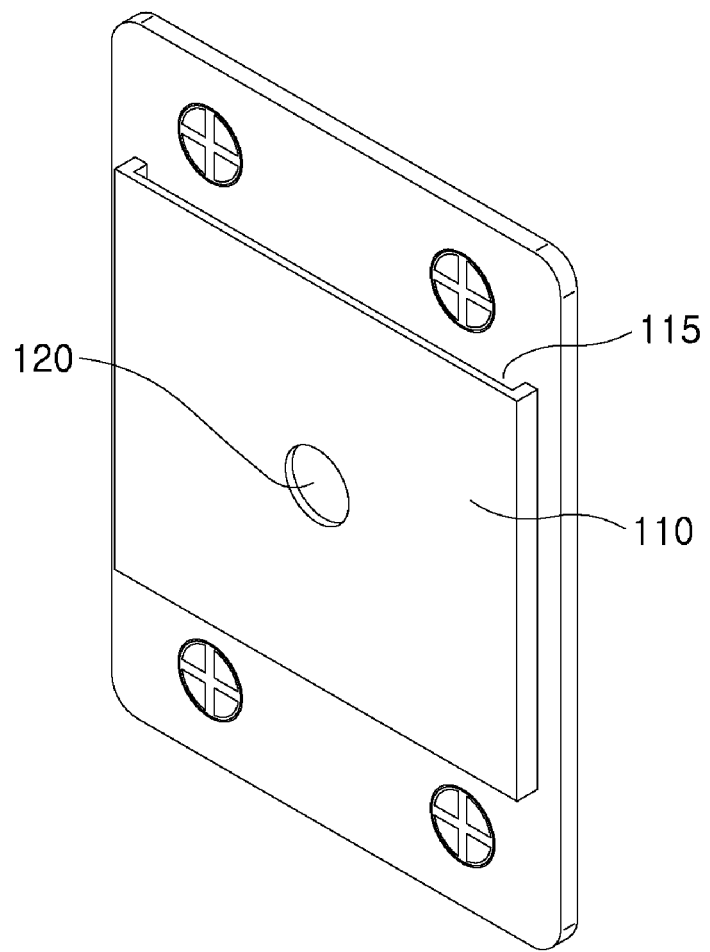
FIG. 5 shows a state in which a fixing apparatus for cervical vertebrae according to an embodiment of the present invention is covered with a cover.

With reference to FIGS. 1 to 5, a fixing system for cervical vertebrae which includes a fixing apparatus for cervical vertebrae according to an embodiment of the present invention will be described. FIG. 1 shows a state in which a fixing apparatus for cervical vertebrae according to an embodiment of the present invention is mounted in the cervical vertebrae, FIG. 2 shows a state in which screw holes of a fixing apparatus for cervical vertebrae according to an embodiment of the present invention are opened, FIG. 3 shows a state in which screw holes of a fixing apparatus for cervical vertebrae according to an embodiment of the present invention are shielded, FIG. 4 is a perspective view showing a driver used for a fixing apparatus for cervical vertebrae according to an embodiment of the present invention, and FIG. 5 shows a state in which a fixing apparatus for cervical vertebrae according to an embodiment of the present invention is covered with a cover.

Referring to FIGS. 1 to 5, the system for fixing cervical vertebrae which includes the fixing apparatus for cervical vertebrae according to an embodiment of the present invention includes the fixing apparatus for cervical vertebrae, a pinion driver 100, an insertion driver, a loosening driver, and a cover 110.

First, the fixing apparatus for cervical vertebrae among the components of the system for fixing cervical vertebrae is constituted of a cervical vertebrae-fixing plate 10 and a screw 130 that is inserted into the cervical vertebrae, and serves to fix cervical vertebrae 5. Specifically, as to the fixing apparatus for cervical vertebrae, a vertebral body in which a lesion is caused is removed, an artificial implant is inserted into a place from which the vertebral body was removed so as to sustain and fix a structural relationship between the inserted artificial implant and the adjacent vertebral body.

The cervical vertebrae-fixing plate 10 may be a plate-shaped metal plate, and a predetermined number of screw holes 20 are formed therein. Through the screw holes 20 formed in the cervical vertebrae-fixing plate 10, the screw 130 may be inserted into the cervical vertebrae 5.

In addition, in the cervical vertebrae-fixing plate 10, an opening and closing member that opens and closes the screw holes 20 while being moved between a closing position for covering the screw holes 20 and an opening position for opening the screw holes on the cervical vertebrae-fixing plate 10 may be provided. The screw holes 20 into which the screw 130 is inserted are shielded by the opening and closing member, and thereby it is possible to prevent the loosening of the screw 130 after cervical vertebrae surgeries, thereby preventing damage to the inside of the body such as esophageal damage due to the loosening of the screw 130. In addition, upon the removal of the inserted screw 130, the opening and closing member may be moved to the opening position and then the screw 130 may be removed.

The pinion driver 100 is a driver that moves the opening and closing member, and a front end portion 90 of the pinion driver 100 has a pinion shape and is in mesh with rack portions 35 and 45 of the opening and closing member to make the rack portions 35 and 45 linearly move, and thereby the opening and closing member is moved on the cervical vertebrae-fixing plate 10.

Hereinafter, the shape and the opening and closing method of the opening and closing member according to an embodiment of the present invention will be described in more detail with reference to FIGS. 1 to 3. Opening and closing members may include covering portions 30 and 40 for covering the screw holes 20 and the rack portions 35 and 45 which are branched from the covering portions 30 and 40 and have teeth thereon. Two opening and closing members may be provided on the cervical vertebrae-fixing plate 10, and moved in opposite directions from each other to shield the screw holes 20.

The teeth of the rack portions 35 and 45 of each of the opening and closing members may face each other, and the pinion driver 100 having the pinion-shaped front end portion 90 may be all engaged with the teeth of the rack portions 35 and 45 and then rotated, so that the rack portions 35 and 45 of each of the opening and closing members linearly move in opposite directions to/from each other, and therefore each of the opening and closing members is moved slidably between the closing position and the opening position on the cervical vertebrae-fixing plate 10 in the same manner as that of a shutter.

In addition, a driver hole 50 in which the pinion driver 100 passes is formed in the cervical vertebrae-fixing plate 10, and the pinion driver 100 which is all engaged with the teeth of the rack portions 35 and 45 may pass the driver hole 50, so that the driver hole 50 may serve as a space for the operation of the pinion driver 100.

In this manner, by moving the opening and closing member between the closing position and the opening position using the pinion driver 100, it is possible to prevent the loosening of the inserted screw 130, and easily move the opening and closing member from the closing position upon the removal of the inserted screw 130, and thereby the removal of the screw 130 is easily performed.

Meanwhile, a position fixing member for preventing a positional change of the opening and closing member is required so that the screw holes 20 are covered with the opening and closing member that has been moved to the closing position, and for this, a fixing groove 140 may be formed between the neighboring screw holes 20 in the transverse direction of the cervical vertebrae-fixing plates 10 and 70 on the cervical vertebrae-fixing plates 10 and 70, and a latching protrusion 145 may be formed in the covering portions 30 and 40 of the opening and closing member to correspond to the fixing groove 140.

That is, the opening and closing member is moved to the screw holes 20 to shield the screw holes 20 and at the same time, the latching protrusion 145 of the opening and closing member is caught in the fixing groove 140 in the cervical vertebrae-fixing plates 10 and 70, and thereby the opening and closing member may continuously shield the screw holes 20 without additional movement thereof.

In some cases, as to the position fixing member, the latching protrusion may be formed on the cervical vertebrae-fixing plate, and the fixing groove may be formed in the opening and closing member. In addition, in both of the above-described two cases of the position fixing member, the fixing groove may have a penetration form or a recessed form that is recessed by only a predetermined depth.

The insertion driver may enable the screw 130 to be inserted into the cervical vertebrae 5 by turning the screw 130, and the shape of a front end portion of the insertion driver may vary depending on the shape of a groove in the screw head of the screw 130 to be used, but the front end portion of the insertion driver may have a hexagonal or star-like shape. In addition, the loosening driver is a driver that loosens the screw 130 inserted into the cervical vertebrae 5, and may have the same shape as that of the insertion driver.

In addition, the system for fixing cervical vertebrae may further include the cover 110, and the cover 110 provided on the cervical vertebrae-fixing plate 10 may serve to cover at least a part of the opening and closing member. An opening portion 115 may be formed on a side surface in the transverse direction of the cover 110, and thereby the at least a part of the opening and closing member may be covered with the cover 110 when the opening and closing member is positioned in the opening position, but when being moved to the closing position, the opening and closing member may emerge from the cover 110 through the opening portion 115 of the cover 110 and then may be moved to the closing position in which the screw holes 20 are positioned.

A cover hole 120 may be formed in the upper surface of the cover 110, so that the pinion driver 100 may be inserted into the cover 110 through the cover hole 120.

The inserted pinion driver 100 is engaged with the teeth of the rack portions 35 and 45 and then rotated, so that the rack portions 35 and 45 are moved, and accordingly, the opening and closing members are moved between the closing position and the opening position on the cervical vertebrae-fixing plate 10.

In addition, the cover 110 may be made of a transparent material, and in this case, it is possible to easily observe the position and movement of the opening and closing member from the outside, and observe whether the pinion driver and the rack portions are accurately engaged with each other.

Meanwhile, in some cases, the cover may cover the screw holes in addition to the opening and closing member, and in these cases, the cover is made of a transparent material, so that the position and movement of the opening and closing member may be observed, and therefore, when a problem in the movement occurs, it is possible to quickly find the problem and properly cope with the problem.

As above, the system for fixing cervical vertebrae according to an embodiment of the present invention has been described, and hereinafter, a fixing system for cervical vertebrae according to another embodiment of the present invention will be described. The system for fixing cervical vertebrae according to another embodiment of the present invention may further include a latching member 80 that restricts the movement of the opening and closing member. Specifically, in the system for fixing cervical vertebrae according to another embodiment of the present invention, the latching member 80 that prevents the opening and closing member from being further moved even after the opening and closing member is moved to shield the screw holes 20 is formed on the cervical vertebrae-fixing plate 70. The formation position and shape of the latching member 80 may vary as long as it can restrict the movement of the opening and closing member, but by way of an example, the latching member 80 may be positioned at the rear of the screw holes 20 relative to the movement direction of the opening and closing member.

The latching member 80 will be described in more detail with reference to FIG. 6. The latching member 80 is positioned at the rear of the screw holes 20, has a rod shape which is long in the transverse direction of the cervical vertebrae-fixing plate 70, and protrudes from the cervical vertebrae-fixing plate 70. Since the latching member 80 protrudes from the cervical vertebrae-fixing plate 70, it is possible to prevent the opening and closing member from being further moved from the closing position in which the opening and closing member shields the screw holes 20, and particularly even when the cervical vertebrae-fixing plate 70 is covered with the cover 110 so that the movement of the opening and closing member cannot be observed, the latching member 80 blocks the undesirable movement of the opening and closing member, thereby effectively controlling the movement of the opening and closing member.

As above, the system for fixing cervical vertebrae according to an embodiment and another embodiment of the present invention has been described, and hereinafter, a fixing system for cervical vertebrae according to still another embodiment of the present invention will be described. In a case of the system for fixing cervical vertebrae according to still another embodiment of the present invention, a clip is formed in the screw holes 20 of the cervical vertebrae-fixing plate.

Figure 6:
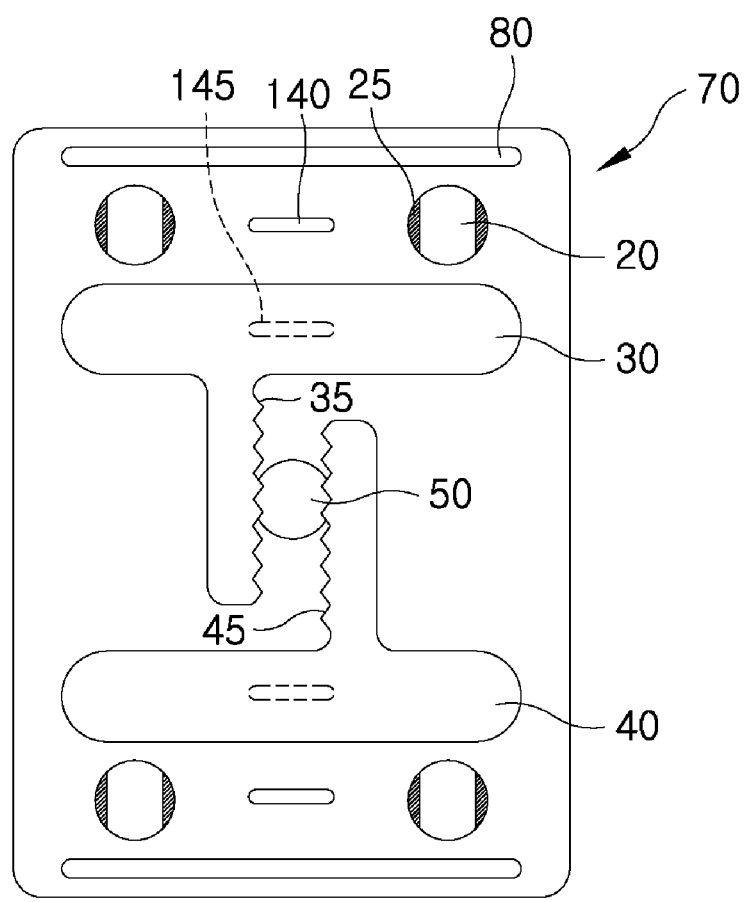
FIG. 6 shows a fixing apparatus for cervical vertebrae according to another embodiment of the present invention.

Specifically, referring to FIG. 6, a clip 25 is provided in each of the screw holes 20, and prevents the separation of the screw 130 when easily shaken or such as escaping backward while holding the screw 130 inserted into the cervical vertebrae 5. As to a structure in which the clip 25 is provided in the screw holes 20, two clips 25 may be provided in positions facing each other on the circumference of the screw holes 20, and the provided clips 25 may protrude from the inner circumference of the screw holes 20. In some cases, the number of the clips to be provided and the position of the clips to be provided on the circumference may vary.

In addition, when the clips 25 are provided in the screw holes 20, the loosening driver of the system for fixing cervical vertebrae according to still another embodiment of the present invention has a convex portion formed at the rear of a front end portion thereof, which is fitted into grooves on the screw 130. The convex portion may have a shape which ascends from a starting portion thereof towards a peak thereof and then descends from the peak towards a distal end portion thereof, and the cross-section of the convex portion may have an oval shape.

As to the sizes of the convex portion of the loosening driver, a distance between peaks out of the convex portion, which are vertically farthest from the main body of the loosening driver and symmetrical to each other, that is, a major axis of the cross-section having the largest area among the cross-sections of the oval-shaped convex portion may be equal to a diameter of the screw hole 20 of the cervical vertebrae-fixing plate or a diameter of the screw head. In addition, a minor axis of the cross-section having the largest area among the cross-sections of the oval-shaped convex portion may be equal to a distance between both clips provided to face each other on the circumference of the screw hole 20.

In this manner, the loosening driver may have the convex portion formed in the front end portion thereof, and the convex portion may spread the clips 25 due to the above-described sizes of the cross-sections of the convex portion while the screw 130 is loosened, and thereby the removal of the screw 130 may be facilitated. Specifically, the front end portion of the loosening driver is fitted into the groove of the screw 130 which is held by the clips 25, and then the screw 130 is loosened by turning the loosening driver and at the same time the convex portion of the loosening driver spreads the clips 25, so that the pressure applied to the screw 130 by the clips 25 may be removed, and thereby the loosening or removal of the screw 130 inserted into the cervical vertebrae 5 may be facilitated.

A fixing apparatus for cervical vertebrae according to yet another embodiment of the present invention will be described with reference to FIG. 6. FIG. 6 shows a fixing apparatus for cervical vertebrae according to yet another embodiment of the present invention.

Referring to FIG. 6, in a case of the fixing apparatus for cervical vertebrae according to yet another embodiment of the present invention, the opening and closing member for covering the screw holes 20 is provided in the cervical vertebrae-fixing plate 70, and the latching member 80 for restricting the movement of the opening and closing member is formed at the rear of the screw holes 20. In addition, the clips 25 are provided in the screw holes 20.

That is, the fixing apparatus for cervical vertebrae according to yet another embodiment of the present invention corresponds to an embodiment including all of the characteristic features of the above-described apparatus for fixing cervical vertebrae.

As described above, according to the embodiments of the present invention, the system for fixing cervical vertebrae may include the loosening prevention member that can prevent the loosening of a screw inserted into the cervical vertebrae and may be easily moved only with a simple operation so that the inserted screw can be easily removed.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An apparatus for cervical vertebrae, the apparatus comprising a fixing plate having a configuration to be located in proximity with the cervical vertebrae, the fixing plate comprising:
   at least one screw hole in which a screw has a configuration to be inserted into the cervical vertebrae therethrough, and
   a sliding cover movable between an open position and a closed position opening and closing the at least one screw, wherein the at least one screw hole comprises a first pair of screw holes and a second pairs of screw holes located in opposite direction from one another,
   wherein the sliding cover comprises a first sliding cover and a second sliding cover, and
   wherein when the sliding cover is in the closed position, both of the first pair and the second pair of screw holes are entirely covered by the first sliding cover and the second sliding cover, respectively.

2. The apparatus of claim 1, wherein the sliding cover comprises:
   a covering portion entirely covering both of the first pair of screw holes and the second pair of screw holes when the sliding cover is in the closed position, and
   a rack portion extended from the covering portion and having teeth thereon.

3. The apparatus of claim 2, further comprises a fixed cover that is attached to the fixing plate and has a hole,
   wherein the hole receives a pinion driver having a pinion-shaped front end portion and is formed at a location that the pinion driver engages and rotates with the teeth of the rack portion.

4. The apparatus of claim 3, wherein the fixed cover is made of a transparent material.

5. The apparatus of claim 4, wherein the fixed cover has an opening portion on a side, and when the sliding cover is in the closed position, a portion of the sliding cover moves out from the fixed cover through the opening portion.

6. The apparatus of claim 3, wherein the fixed cover covers a portion of the sliding cover.

7. The apparatus of claim 1, wherein each of the first sliding cover and the second sliding cover moves in opposite directions from one another to cover the first pairs and the second pairs of screw holes, respectively.

8. The apparatus of claim 7, wherein the first sliding cover comprises a first rack portion having a first teeth thereon, and the second sliding cover comprises a second rack portion having a second teeth thereon, and wherein the first rack portion and the second rack portion are disposed to face each other, and the first rack portion and the second rack portion move between the open position and the closed position as a pinion driver having a pinion-shaped front end portion engages and rotates with the first teeth and the second teeth in a first direction and a second direction opposite to the first direction.

9. The apparatus of claim 8, wherein the fixing plate further comprises a driver hole thereon, wherein the driver hole receives the pinion driver, and wherein the pinion driver engages with the first teeth and the second teeth and rotates with respect to a center of the driver hole.

10. The apparatus of claim 1, wherein the fixing plate further includes a locking protrusion preventing the sliding cover from a movement when the sliding cover is in the closed position.

11. The apparatus of claim 10, wherein when the sliding cover is in the open position, the at least one screw hole is located between the locking protrusion and the sliding cover.

12. The apparatus of claim 1, wherein the fixing plate further includes a clip located on a circumference of the at least one screw hole and holds the screw.

13. The apparatus of claim 1, wherein a fixing groove is formed on the fixing plate adjacent to the at least one screw hole, and a latching protrusion is formed on the sliding cover at a location corresponding to the fixing groove when the sliding cover is in the closed position.

14. A system comprising:
an apparatus for cervical vertebrae, the apparatus comprising a fixing plate having a configuration to be located in proximity with the cervical vertebrae, the fixing plate comprising:
at least one screw hole in which a screw has a configuration to be inserted into the cervical vertebrae there-through, wherein the at least one screw hole comprises a first pair of screw holes and a second pairs of screw holes located in opposite direction from one another, and
a sliding cover movable between an open position and a closed position opening and closing the at least one screw, wherein the sliding cover comprises a first sliding cover and a second sliding cover,
wherein the sliding cover comprises a covering portion entirely covering both of the first pair and the second pair of screw holes by the first sliding cover and the second sliding cover, respectively when the sliding cover is in the closed position, and a rack portion extended from the covering portion and having teeth thereon,
wherein the rack portion moves between the open position and the closed position as a pinion driver having a pinion-shaped front end portion engages and rotates with the teeth in a first direction and a second direction opposite to the first direction.

15. The system of claim 14, wherein each of the first sliding cover and the second sliding cover moves in opposite directions from one another to cover the at least one of the first pair of screw holes and the second pair of screw holes.

16. The system of claim 15, wherein the first sliding cover comprises a first rack portion having a first teeth thereon, and the second sliding cover comprises a second rack portion having a second teeth thereon, and wherein the first rack portion and the second rack portion are disposed to face each other, and the first rack portion and the second rack portion move in opposite directions between the open position and the closed position as the pinion driver engages and rotates with the first teeth and the second teeth in the first direction and the second direction opposite to the first direction.

* * * * *